United States Patent [19]

Loomis

[11] Patent Number: 5,170,781

[45] Date of Patent: Dec. 15, 1992

[54] PROTECTIVE BANDAGE HAVING IMPROVED IMPACT PROTECTION

[76] Inventor: Dawn L. Loomis, 475 Newport, Naperville, Ill. 60565

[21] Appl. No.: 794,724

[22] Filed: Nov. 15, 1991

[51] Int. Cl.⁵ .......................... A61F 5/30; A61F 5/34; A61F 13/00; A61L 15/00
[52] U.S. Cl. ............................ 128/118.1; 128/117.1; 128/888; 128/893; 128/894; 602/41; 602/42; 602/58
[58] Field of Search ........... 128/99.1, 106.1, DIG. 20, 128/111.1, 112.1, 117.1, 118.1, 155, 865, 888, 889, 895, 894; 602/41, 42, 53, 58, 59, 60–66, 75, 77

[56] References Cited

U.S. PATENT DOCUMENTS

| | | | |
|---|---|---|---|
| 1,913,928 | 6/1933 | Kaufman | 128/894 |
| 3,171,410 | 3/1965 | Towle, Jr. et al. | 128/118.1 |
| 4,224,945 | 9/1980 | Cohen | 128/155 |
| 4,962,769 | 10/1990 | Garcia | 128/889 |
| 4,964,858 | 10/1990 | Livny | 128/D 20 |

*Primary Examiner*—David Isabella
*Assistant Examiner*—A. Zuttarelli
*Attorney, Agent, or Firm*—Dressler, Goldsmith, Shore, Sutker & Milnamow, Ltd.

[57] ABSTRACT

A protective bandage for covering a wound or other sensitive body area. A fluid-filled bubble means is positioned centrally of the bandage and is adapted to overlie the sensitive body area to protect it against impacts, to reduce the pain of impacts, and to promote healing.

3 Claims, 1 Drawing Sheet

PROTECTIVE BANDAGE HAVING IMPROVED IMPACT PROTECTION

BACKGROUND OF THE INVENTION

Protective bandages are widely used for covering wounds and sensitive body areas. Some such bandages typically comprise an elongated patch or strip which usually has an associated gauze pad or the like which overlies the sensitive area and which serves to permit air flow and promote healing. Typical bandages of this type are shown in U.S. Pat. Nos. 2,858,830; 2,992,644; and U.S. Pat. No. 3,113,568. Although the gauze or like material of such a bandage provides modest cushioning, it fails to provide protection against sharp impacts or repeated impacts due to a wide variety of environmental conditions.

It would be of advantage to athletes and to a broad universe of users of protective bandages to provide for substantially enhanced resistance to inflicting additional injury to, or causing pain in, a sensitive body area, such as a preexisting wound, blistered area or the like, by impacts from a variety of sources.

SUMMARY OF THE INVENTION

In accordance with the present invention, an improved protective bandage for covering a sensitive body area and having improved impact resistance is provided. The improved bandage comprises an anchoring strip comprising a main body and an adhesive surface on one side of the main body for securing the strip to a body area, and a fluid-filled bubble means located generally centrally of the strip and adapted to be positioned and maintained over a sensitive body area via the adhesive surface, thereby to protect a sensitive body area from the shock of impacts. Preferably the bubble means is an air-filled bubble and is formed from a laminate of a pair of sheets defining an air pocket, which laminate is secured to the anchoring strip. In another form of the invention, the bubble means comprises a laminate of the strip and a sheet laminated thereto, which together define an air pocket therebetween. The strip may desirably be elongated and define a non-adhesive zone centrally of the strip on one side of the main body, with the bubble being disposed on the other side of the main body over the non-adhesive zone. A single bubble or a small plurality of bubbles may be used.

Further objects, features and advantages of the present invention will be apparent from the foregoing, and from the following description and drawings.

DESCRIPTION OF THE PREFERRED EMBODIMENTS

Figure 1:
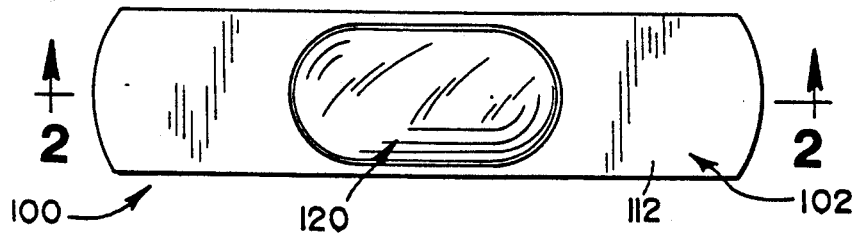
FIG. 1 is a plan view of a protective bandage in accordance with the present invention.

Referring now to the drawings, a presently preferred protective bandage 100 for covering a sensitive body area and having improved impact resistance has an anchoring or backing strip 102 and an adhesive layer such as a pressure sensitive adhesive layer 104 on one side of the main body of the strip for securing the strip to a body area. The backing strip may comprise a conventional plastic strip or fabric strip, such as the relatively elongated strip shown. Other shapes and relative dimensions for the bandages and the strips may be used as well. A pad 106 of absorbent material is provided generally centrally of the strip. The pad may comprise conventional materials well known for such purposes. The surface 108 of the pad 106 is non-adhesive. The body of the strip 102 may be perforated in a conventional manner to allow the bandage to breath.

As is conventional, cover strips 110 having release surfaces which readily release from the pressure sensitive adhesive layer 104 are provided for removal from the surfaces of the adhesive layer 104 immediately prior to application to a body area to which the bandage is to be secured.

Figure 2:
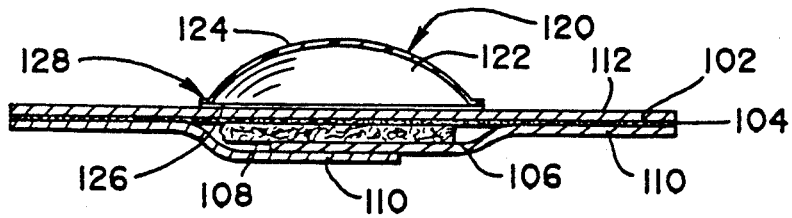
FIG. 2 is a cross-sectional view of the protective bandage of FIG. 1, taken substantially along line 2—2 of FIG. 1.
Figure 3:
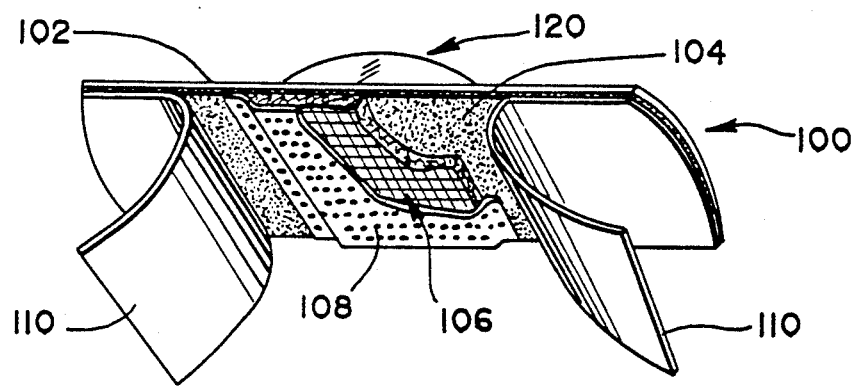
FIG. 3 is a perspective view of the protective bandage of FIG. 1.

In accordance with the present invention the bandage 100 is provided with a fluid-filled bubble means, such as the bubble 120 illustrated in FIGS. 2 and 3 which is filled with air 122. Bubble 120 may be a laminate, and may be formed of a pair of plastic sheets 124, 126 which are laminated to each, as with a suitable adhesive about their peripheries 128 to define an air pocket within the peripheries. Alternatively, the bubble 120 may be formed by heat sealing two thin plastic sheets, such as air impervious polyethylene sheets, to each other around their peripheries, one sheet being substantially flat and the other being domed at the time of lamination with air being trapped between them, as in a manner conventionally employed in making bubble packaging used for wrapping and protecting products to be shipped.

Bubbles so formed may then be bonded, as with a suitable adhesive, such as a pressure sensitive adhesive, to the surface 112 of the backing strip generally centrally of the strip, such as in a position overlying the pad 106.

It will be apparent from FIGS. 1 to 3 that the air-filled bubble may be a single bubble which is preferably sufficiently filled so that even impact by a relatively pointed object will resist direct contact against the main body of the backing strip 102, hence will protect the underlying sensitive body area. Desirably it should be at least about ⅛" in height. Preferably the bubble is not overfilled. As such it will tend to conform to a contacting surface confronting the bandage, while maintaining some space between the outer surface of the bubble and the backing strip, thereby to minimize impacts against an underlying sensitive body area. Thus, for example, if an athletic shoe surface bears against the bubble, that shoe surface will remain spaced from the backing strip in the zone of the bubble to resist abrasion and impact by the shoe against an underlying sensitive body area, such as a blistered area. By protecting the sensitive body area against impact, the bandage promotes more rapid healing.

Figure 4:
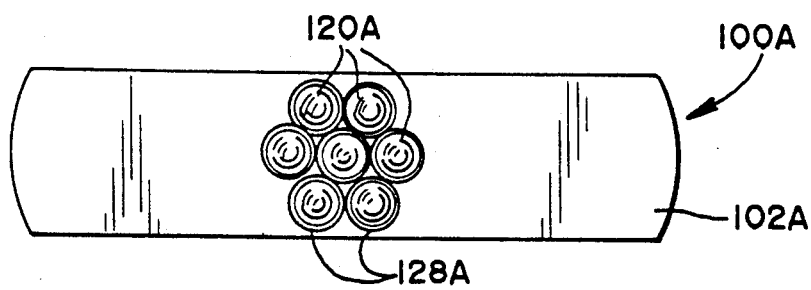
FIG. 4 is a plan view of another embodiment of the present invention.

As shown by FIG. 4, a bandage 100A having a backing strip 102A may have a bubble means which comprises a small plurality or series of smaller bubbles 120A, each of which is fluid or air-filled and which defines a laminated periphery or border 128A. The smaller bubbles should be positioned in a tightly packed array and may be in the range of about 9 to about 25 bubbles per square inch. The materials used and methods used to make the impact resistant fluid-filled cushion formed of the series of the smaller bubbles 120A may be the same as that used to make the bubble 120 of the embodiment of FIGS. 1 to 3.

Figure 5:
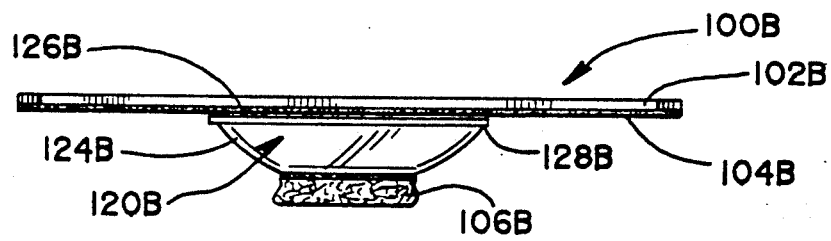
FIG. 5 is a cross-sectional view, like that of FIG. 2, of a further embodiment of the present invention.
Figure 6:
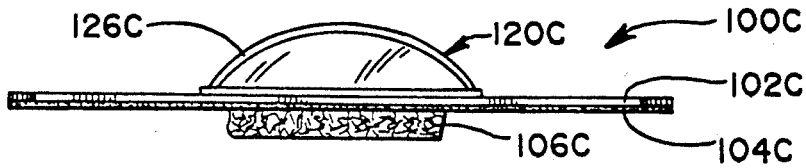
FIG. 6 is a cross sectional view, like FIG. 5, of yet another embodiment of the present invention.

Although the preferred form of the invention positions the fluid-filled bubble on the outside of the bandage, namely on the side of the backing strip opposite the pad, it is also possible to affix the bubble to the inside of the bandage, either directly to the surface of the pad so that the bubble bears directly against the sensitive area or between the backing strip and a pad. The latter embodiment is illustrated by FIG. 5 in which a bandage 100B having a backing strip 102B has an adhesive layer 104B to which a bubble 120B made of a laminate like bubble 120 and having sheets 124B, 126B and a periphery 128B is secured to the strip by adhesive 104B. A pad 106B is adhesively secured to the bubble 120B.

In yet another form of the present invention, a bubble may be fabricated by laminating a sheet of plastic material directly to a backing strip. In that instance, the plastic sheet material would typically define the domed portion of the laminate and the backing strip would serve as the generally flat sheet. Lamination would be accomplished by adhering the strip and sheet together or by heat sealing them, depending on the materials of which the backing strip is made. In this form a bandage 100C would include a backing strip 102C, an adhesive layer 104C, a pad 106C, and a bubble 120C. As explained, bubble 120C is formed from a sheet 126C laminated to the backing strip 102C.

It will be apparent to those skilled in the art that further modifications may be made in the invention as described without departing from the spirit and scope of the present invention. Accordingly, I do not intend to be limited to the illustrated embodiments, except to the extent made necessary by the appended claims.

What is claimed is:

1. A protective strip bandage for covering a sensitive body area and having improved impact resistance comprising:

an anchoring strip defining marginal edges comprising a main sheet having two sides and an adhesive surface on one of the sides of the main sheet for securing the strip to a body surface;

a fluid-filled bubble means located general centrally of the strip and within the marginal edges of said strip and adapted to be positioned and maintained over a sensitive body area by adherence of said adhesive surface to the body surface to protect the sensitive body area from impacts thereagainst, said bubble means comprising a laminate of a pair of sheets, and wherein said bubble mean comprises a plurality of individual bubbles of up to b 25 closely packed bubbles per square inch, and wherein said strip is elongated and defines a non-adhesive zone centrally of the adhesive surface of the strip on said one side of the main sheet and said bubble means is disposed on the other of said sides of said main sheets over said non-adhesive zone.

2. A protective bandage in accordance with claim 1, and wherein said fluid-filled bubble means is air-filled.

3. A protective strip bandage in accordance with claim 1, and wherein said pair of sheets are thin, heat-sealed plastic sheets defining said plurality of bubbles.

* * * * *